United States Patent
Berk et al.

(10) Patent No.: US 8,119,375 B2
(45) Date of Patent: Feb. 21, 2012

(54) METHOD FOR THE PRODUCTION OF RAMIPRIL

(75) Inventors: Holger Berk, Niederaula-Hattenbach (DE); Frank Zocher, Frankfurt am Main (DE); Hans-Wolfram Flemming, Frankfurt am Main (DE); Rainer Gauler, Frankfurt am Main (DE); Rudolf Lehnert, Frankfurt am Main (DE); Wolfgang Laux, Paris (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 545 days.

(21) Appl. No.: 12/142,095

(22) Filed: Jun. 19, 2008

(65) Prior Publication Data

US 2009/0017509 A1 Jan. 15, 2009

Related U.S. Application Data

(63) Continuation of application No. PCT/EP2006/011891, filed on Dec. 11, 2006.

(30) Foreign Application Priority Data

Dec. 21, 2005 (DE) .......................... 10 2005 061 756

(51) Int. Cl.
*C12P 17/10* (2006.01)
*C09B 5/00* (2006.01)
*C07C 229/00* (2006.01)
(52) U.S. Cl. ........................... 435/121; 548/416; 560/41
(58) Field of Classification Search .................. 435/121; 548/416; 560/41
See application file for complete search history.

(56) References Cited

U.S. PATENT DOCUMENTS 5,061,722 A   10/1991   Teetz et al.

FOREIGN PATENT DOCUMENTS

| EP | 1502914 | 2/2005 |
|---|---|---|
| WO | WO 2005-049567 | 6/2005 |
| WO | WO 2005-049568 | 6/2005 |

OTHER PUBLICATIONS

Carboni, et al., Quantitative enzymatic protection of d-amino acid methyl esters by exploiting 'relaxed' enantioselectivity of penicillin-G amidase in organic solvent, Tetrahedron Let. 2004; 45(52); p. 9651.

*Primary Examiner* — Herbert J Lilling
(74) *Attorney, Agent, or Firm* — Scully, Scott, Murphy & Presser, P.C.

(57) ABSTRACT

An improved method for preparing ramipril is disclosed, and also an intermediate for use in the method.

6 Claims, No Drawings

METHOD FOR THE PRODUCTION OF RAMIPRIL

The present invention relates to an improved method for preparing ramipril, and to the intermediate used in the method and the use thereof.

Ramipril is an ACE inhibitor which is frequently employed in pharmacy. The methods published to date for preparing ramipril (see, for example, U.S. Pat. No. 5,061,722) are very complicated. Special methods for preparing ACE inhibitors are known (see, for example, European patent applications EP 0215335 and EP 0967221), but lead to other ACE inhibitors or provide no solutions in relation to enantiomer-specific synthesis. With the intention of providing an improved method for preparing ramipril, a method with which it is possible to improve the preparation of ramipril with simple means has now surprisingly been found.

The invention accordingly relates to a method for preparing ramipril, a compound of the formula (I)

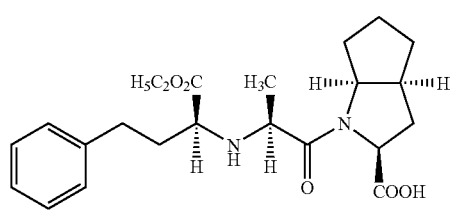

which comprises (A) hydrolyzing a compound of the formula (II)

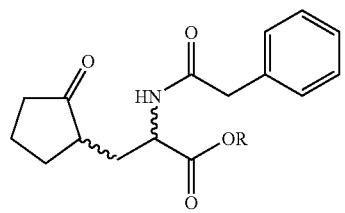

in which R is $(C_1-C_4)$-alkyl, in a suitable solvent with the addition of one or more bases or acids to a compound of the formula (III)

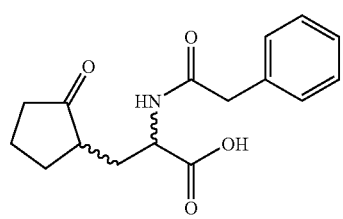

and then (B) converting the compound of the formula (III) under the influence of penicillin G amidase into a mixture of the compounds of the formulae (IV) and (V)

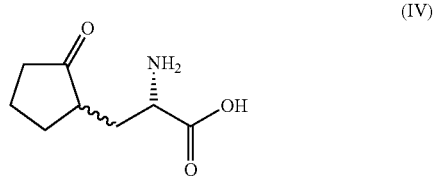

or a mixture of salts of the compounds of the formula (IV) and (V), which are in equilibrium with one another, and then (C) converting the compound (V) or a salt of the compound (V) from the mixture of the compounds (IV) and (V) or salts thereof by catalytic hydrogenation into a compound of the formula (VI)

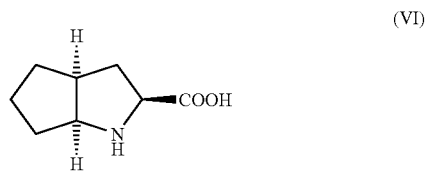

or a salt thereof, and then either (D-A) reacting the compound of the formula (VI) with a compound of the formula (VII)

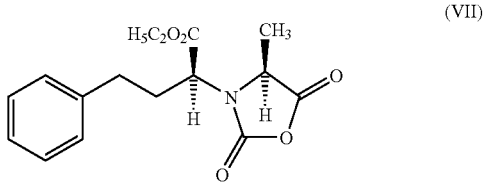

to give the compound of the formula (I), or alternatively (D-B.1) reacting compound (VI) with benzyl alcohol to give a compound of the (VIII)

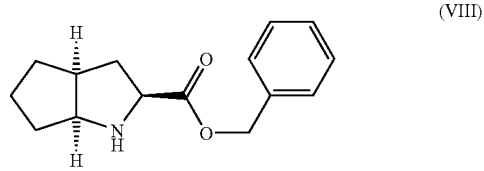

or a salt thereof, and then (D-B.2.1) reacting compound (VIII) either with a compound of the formula (VII) to give a compound of the formula (X)

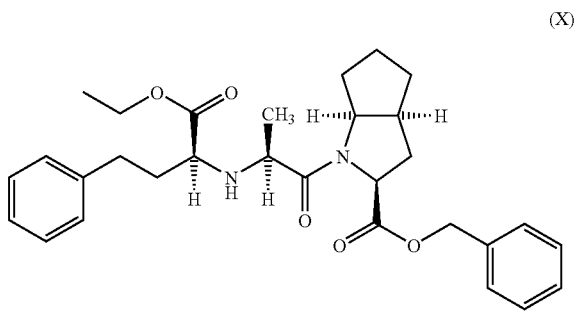

or alternatively (D-B.2.2) reacting the compound (VIII) with a compound of the formula (IX)

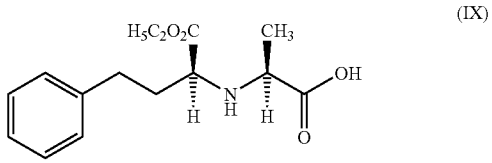

to give the compound (X), and then (D-B.3) forming the compound of the formula (I) from the compound (X) by catalytic hydrogenation.

$(C_1$-$C_4)$-Alkyl means methyl, ethyl, n-propyl, isopropyl, n-butyl, isobutyl or tert-butyl.

Particularly advantageous substeps of the method of the invention consist of steps (B) and (BA') in which a compound having a racemic structural element is converted through the use of penicillin G amidase into a reaction product having a corresponding isomerically pure structural element. The present invention likewise relates to each of these substeps.

The present invention further relates to a method for preparing the compound (I) starting from the compound (III) comprising substeps (B), (C) and either (D-A) or alternatively (D-B.1), (D-B.2.1) or (D-B.2.2) and (D-B.3) as defined above.

The present invention further relates to the intermediate of the formula (II)

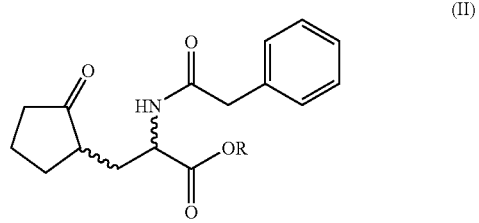

where R is $(C_1$-$C_4)$-alkyl. The compound of the formula (II) in which R is $CH_3$ is particularly important. The compound of the formula (II) in which R is methyl can be prepared for example by (1.) reacting serine methyl ester hydrochloride with phenylacetyl chloride in the presence of a base, e.g. $Na_2CO_3$, in a suitable solvent, e.g. ethyl acetate and/or diisopropyl ether, to give N-phenylacetylserine methyl ester, for example as described by Couloigner et al. (Bioorg. & Med. Chem. Lett. 1999, 9, 2205-2206), (2.) chlorinating the compound obtained in this way under standard conditions, for example with $PCl_3$ or thionyl chloride, in a suitable solvent, e.g. ethyl acetate, for example as described by Anderson et al. (Synthesis 1976, 398-399), and (3.) reacting the methyl 3-chloro-2-phenylacetylaminopropionate obtained in this way with 1-cyclopent-1-enylpyrrolidine (CAS Registry No. 7148-07-4) in the presence of a base, e.g. $NEt_3$, in a suitable solvent, e.g. ethyl acetate, and subsequent acidic working up with, for example, HCl in ethyl acetate, for example as described by Teetz et al., Tetrahedron Lett. 1984, 25(40), 4479-4482. The compound of the formula (II) in which R is methyl can alternatively prepare for example by (1.) chlorination of serine methyl ester hydrochloride with, for example, $PCl_5$ in a suitable solvent, e.g. $CH_2Cl_2$, (2.) reacting the methyl 2-amino-3-chloroopropionate hydrochloride obtained in this way with phenylacetyl chloride in a suitable solvent, e.g. toluene, and (3.) reacting the methyl 3-chloro-2-phenylacetylaminopropionate obtained in this way with 1-cyclopent-1-enylpyrrolidine (CAS Registry No. 7148-07-4) in the presence of a base, e.g. $NEt_3$, in a suitable solvent, e.g. ethyl acetate, and subsequent acidic working up with, for example, HCl in ethyl acetate, for example as described by Teetz et al., Tetrahedron Lett. 1984, 25(40), 4479-4482. The other esters can be prepared in analogy to the procedures mentioned above or are obtainable by transesterification of the methyl ester. Compound (II) is preferably in the form of a mixture of two diasteomeric racemates.

The present invention further relates to the intermediate of the formula (III)

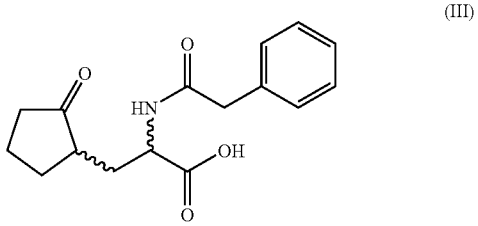

The compound of the formula (III) is prepared in step (A) by hydrolyzing a compound of the formula (II). This can take place by methods known to the skilled worker, for example by introducing the compound of the formula (II) into a suitable solvent, and firstly adding one or more bases, for example NaOH and/or KOH, preferably NaOH, and then adjusting a pH in the range from 6 to 7 by adding acid, preferably HCl. An alternative possibility is firstly to hydrolyze using one or more acids, for example hydrochloric acid, hydrobromic acid, sulfuric acid or methanesulfonic acid, preferably hydrochloric acid, and then to adjust a pH of 6-7 by adding alkali. Suitable solvents are water or water mixed with an organic solvent such as, for example, THF or dioxane. It is possible to isolate the compound of the formula (III). However, in the method of the invention for preparing the compound of the formula (I) it is preferred to process the compound of the formula (III) further in situ. Compound (III) is preferably in the form of a mixture of two diastereomeric racemates.

Step (B) of the method of the invention can take place by introducing the compound of the formula (III) into aqueous solution, and adding penicillin G amidase (E.C. 3.5.1.11). The enzyme penicillin G amidase is used for the industrial preparation of semisynthetic penicillin antibiotics, in which case it catalyzes the hydrolysis of penicillin G to 6-aminopenicillanic acid (6-APA) and phenylacetic acid. Penicillin G amidase is further used in the preparation of cephalosporin antibiotics, in which case it catalyzes the hydrolysis of cephalosporin G to 7-aminodeacetoxycephalosporanic acid (7-ADCA) and phenylacetic acid. The enzyme can be employed immobilized or non-immobilized, and an enzyme immobilized by a carrier material is preferably employed. A large number of possible carrier materials are known to the skilled worker, for example amino-activated silicates (Burteau et al., FEBS Letters (1989), 258(2), 185-189), DEAE-Cellulose (Warburton et al., Biochimica et Biophysica Acta, Enzymology (1972), 284(1), 278-84), Polyurethane (French patent application FR 2371470), macroporous carriers (German patent application DE 3515252) or "aminofunctional organosiloxane polymers" (U.S. Pat. No. 5,780,260). The penicillin G amidase immobilized on amino-functional organosiloxane polymers prepared as described in U.S. Pat. No. 5,780,260 is preferably used in the method of the invention. The ratio by weight of compound of the formula (III) to immobilized penicillin G amidase should in this case be in the ratio 5:1 to 3:1 (e.g. PGA 450 from Roche Diagnostics, order number 1414208; likewise possible are for example PGA beads from Recordati or Fermase PA 1500 or Fermase PA 750 from Fermenta Biotech Ltd. (India)), where the weight of the amidase is based on the enzyme in polymer-bound form. An alternative possibility is also to use a penicillin G amidase supplied by FLUKA (order number 76428: penicillin G amidase, immobilized by E. coli, ~150 U/g as moist material, where 1 U corresponds to the amount of enzyme which hydrolyzes 1 μmol of benzylpenicillin per minute at pH 7.6 and 37° C.). The ratio by weight is preferably 4:1. The penicillin G amidase may moreover be in the form of a solution or suspension (e.g. from Roche Diagnostics, order number 1290959) or in crosslinked cells (e.g. Fermase PA 250 from Fermenta Biotech Ltd. (India)). Step (B) of the method can be carried out at various temperatures. A temperature of from 20 to 45° C. is preferred, and a temperature of from 26 to 30° C. is particularly preferred, especially about 28° C. The reaction can be carried out at pH values between 5 and 9.5. A pH between 6 and 7 is preferred, and a pH of 6.4 is particularly preferred. A suitable solvent is water or water mixed with a $(C_1-C_3)$alkanol, preferably water mixed with methanol, ethanol or isopropanol, or acetone, or DMSO. Mixtures of water with isopropanol (50% w/v), acetone (35% w/v), ethanol (30% w/v), methanol (40% w/v) or DMSO (50% w/v), in each case based on the final concentration are preferred.

After the reaction is complete, an organic solvent is added to the reaction mixture and is used to extract the unwanted diastereomers, with the desired stereomers remaining in the aqueous phase. The aqueous phase preferably has a pH which is less than or equal to the isoelectric point of the salt of the compound (IV) or (V) to be purified. Suitable solvents for the extraction are solvents which are slightly miscible or immiscible with water and are known to the skilled worker. Examples of solvents which are slightly miscible or immiscible with water are ethyl acetate, propyl acetate, butyl acetate, $C_4-C_{10}$-alkanols, e.g. n-butanol, methyl ethyl ketone, toluene, diisopropyl ether or heptane. A particularly suitable solvent is ethyl acetate. Extraction of the unwanted isomer preferably takes place after addition of acid, preferably hydrochloric acid. The pH can in this case be adjusted to a value between 0.5 and 5, preferably 1 and 4, and a pH in the region of 2.2 is particularly suitable. After the phase separation it may be expedient to extract the aqueous phase again one or more times with the relevant organic solvent. The immobilized enzyme can be reused after completion of the reaction and after the extraction.

An alternative possibility is to employ compound (II) as starting material for the enzymatic reaction, in which case the subsequent hydrolysis likewise results in a mixture of the compounds of the formula (IV) and (V) or a mixture of salts of compounds of the formula (IV) and (V), and in which case the pH is between 6.5 and 9.5, preferably 7.5 to 8.5, and the other conditions correspond to those mentioned for step (B) of the method. Following the enzymatic reaction of the compound (II), the resulting, desired, esterified diastereomer is hydrolyzed, with the conditions corresponding to those mentioned for step (A) of the method. This step of the method is called (BA') comprehensively hereinafter. The present invention therefore relates further to a method for preparing the compound (I) starting from the compound (II) comprising substeps (BA'), (C) and either (D-A) or alternatively (D-B.1), (D-B.2.1) or (D-B.2.2) and (D-B.3) as defined above.

It is possible to employ as aqueous phase in step (B) or (BA') of the method optionally aqueous buffer systems with the appropriate pH ranges which are known to the skilled worker, for example a phosphate buffer for a pH of 8.0.

The present invention further relates to a mixture of the compounds of the formulae (IV) and (V)

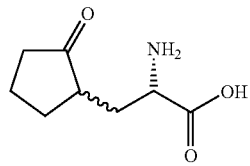

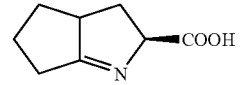

or a mixture of salts of the compounds (IV) and (V), preferably a mixture of the compounds (IV)-HCl and (V)-HCl. The mixture of the compounds (IV) and (V) can optionally be isolated. The mixture of the compounds (VI) and (V) is preferably isolated in the form of an acid addition salt, for example as salt of HCl, HBr, $H_2SO_4$, methanesulfonic acid, toluenesulfonic acid or phenylsulfonic acid. Suitable and preferred for isolating and for triturating the crystals obtained in the working up of the mixture of salts of the compounds (IV) and (V) are water-miscible solvents such as, for example, $(C_2-C_3)$-alkanols or methyl ethyl ketone.

The catalytic hydrogenation in reaction step (C) can be carried out under conditions known to the skilled worker. For example, the method can take place under the following conditions: the aqueous phase of the working up of step (B) or (BA') of the method containing the compound of the formula (V) or a salt thereof mixed with the compound (IV) or a salt thereof is admixed with a suitable catalyst. An example of a suitable catalyst is platinum on activated carbon or palladium on activated carbon, and palladium on activated carbon is particularly suitable. A ratio by weight of palladium to activated carbon of from 5:95 to 10:90) is preferred. The amount of catalyst employed per gram of aqueous solution is preferably 1-10 mg, particularly preferably 3 mg. Further activated carbon can be added to the reaction mixture, preferably 5 to 20 weight units per weight unit of catalyst, particularly preferably 9-13 weight units. The hydrogenation is carried out under a hydrogen pressure of from 5 to 15 bar, preferably from 8 to 12, particularly preferably about 10 bar. The reaction temperature can be between 40° C. and the boiling point of the reaction mixture, and is preferably 60-100° C. A preferred reaction temperature is about 80° C.

The hydrogenation of the compound (V) or a salt thereof from the mixture of the compounds (IV) and (V) shifts the equilibrium between the compounds (IV) and (V) in favor of compound (V) because only compound (V) can be hydrogenated. Compound (VI) can optionally be isolated. The compound (VI) can be isolated in free form or in the form of an acid addition salt, for example as salt of HCl, HBr, $H_2SO_4$, methanesulfonic acid, toluenesulfonic acid or phenylsulfonic acid. Suitable and preferred for the isolation and for the trituration of the in the working up of the compound (VI) or salts of the compound (VI) are water-miscible solvents such as, for example, ($C_2$-$C_3$)-alkanols or methyl ethyl ketone.

The compound (VI) can be liberated from the acid addition salt before the following step (D-A) or (D-B.1) by adding base, for example NaOH or KOH, and then optionally be desalted by electrodialysis.

Following the enzymatic racemate resolution in step (B) or (BA') of the method, the compound (IV) is in the form with (2S,3RS) stereochemistry. In the hydrogenation, it is ensured through the preceding equilibrium of the cyclic form (V) with the open-chain form (IV) and the possible racemization at position 3 (because of a keto-enol tautomerism in acids) that there is formation exclusively of the compound (VI), but not of the diastereomer thereof. The unwanted (3R) isomer of the compound (V) can be hydrogenated only very slowly, because of the steric hindrance on the catalyst surface, so that it is re-isomerized through the open-chain compound (3R)-(IV) with which it is in equilibrium into the (3S)-(IV) isomer which is then hydrogenated further to the all-S bicycle (VI).

Step (D-A) of the method can be carried out under conditions known to the skilled worker, for example as described in U.S. Pat. No. 4,496,541, example 1. The compound (VI) is mixed with the compound (VII) in a suitable solvent, for example dichloromethane or water, at a pH of 8-12, preferably 10-11, and stirred for example at 10-40° C., preferably 20-25° C.

Esterification of the compound (VI) with benzyl alcohol in step (D-B.1) of the method can be carried out by methods known to the skilled worker, for example as described in European patent application EP 79022 A2, example I (3): compound (VI) is optionally activated by initially reacting it with methanesulfonic acid or thionyl chloride in a suitable solvent, for example n-hexane, n-heptane, toluene or a mixture thereof; the optionally activated compound (VI) is then mixed with benzyl alcohol, the reaction preferably being carried out under reflux. The compound (VIII) obtained in this way, benzyl (2S,3aS,6aS)octahydrocyclopenta[b]pyrrole-2-carboxylate, can optionally be isolated.

The compound (VIII) is preferably isolated in the form of an acid addition salt, for example as salts of HCl, HBr, $H_2SO_4$, oxalic acid, phosphoric acid, methanesulfonic acid, toluenesulfonic acid, or phenylsulfonic acid. The compound (VIII) is preferably liberated from the acid addition salt before the following step (D-B.2.1) or (D-B.2.2) by adding base, for example NaOH or KOH.

Step (D-B.2.1) of the method can be carried out by mixing compound (VIII) with compound (VII) in a suitable solvent. Suitable solvents are generally aprotic and water-immiscible solvents, for example butyl acetate, ethyl acetate, dichloromethane and toluene. The temperature of the reaction of (VIII) with (VII) is 5-30° C., preferably 10-15° C. For working up, the reaction mixture can be mixed with an aqueous base, preferably sodium hydroxide solution or potassium hydroxide solution of a pH of 10-13 for aqueous extraction of excess compound (IX) produced by hydrolysis of (VII). The resulting compound (X) can optionally be isolated.

The amide formation in step (D-B.2.2) of the method can be carried out by methods known to the skilled worker, for example as described in European patent application EP 79022 A2, example I (4). The compound of the formula (VIII) is coupled with the compound of the formula (IX) in a suitable inert solvent, for example ethyl acetate, butyl acetate, dichloromethane or dimethylformamide, at a temperature of 5-20° C., preferably 10-15° C., in the presence of one or more standard amide-coupling reagents, for example dicyclohexylcarbodiimide, HOBt, propanephosphonic anhydride or methanephosphonic anhydride, keeping the pH preferably at between 8 and 9, for example by means of sodium hydroxide solution. The compound (X), obtained in this way, benzyl(2S, 3aS,6aS)-1-2-[[(1S)-1-(ethoxycarbonyl)-3-phenylpropyl] amino]-(2S) -propanoyl)octahydrocyclopenta[b]pyrrole-2-carboxylate, is optionally isolated.

The catalytic hydrogenation in step (D-B.3) of the method can be carried out by methods known to the skilled worker, for example as described in European patent application EP 79022 A2, example I (5). The benzyl ester of the formula (X) is cleaved for example by catalytic hydrogenation, with the hydrogenation being catalytically hydrogenated preferably in a suitable solvent, e.g. a ($C_1$-$C_3$)alkanol, preferably methanol or ethanol, at a temperature of 0-20° C., preferably 5-10° C., under a pressure of 0.5-3 bar, preferably under 1.0-2.0 bar, with addition of a suitable catalyst, e.g. Pd/C (10% by weight).

The compound of the formula (I) can optionally be purified further by standard methods following steps (D-A) or (D-B.3) of the method, for example by chromatographic methods or by recrystallization from a suitable solvent. A suitable solvent is for example a mixture of methanol and diisopropyl ether, or alternatively acetone, or ethyl acetate.

The present invention is to be illustrated, but not restricted, by the following exemplary embodiments.

EXAMPLE 1

Preparation of the Compound of the Formula (II) with R Equal to methyl, (3-(2-oxocyclopentyl)-2-phenylacetylaminopropionate), Starting from methyl 3-chloro-N-phenylacetylalaninate 16 g of methyl 3-chloro-N-phenylacetylalaninate were suspended in 100 ml of ethyl acetate. At 20-25° C., 20 ml of triethylamine were added and immediately thereafter 18 g of 1-cyclopent-1-enylpyrrolidine were added dropwise at 20-30° C. over the course of 20 minutes. The mixture was heated to 40-45° C. and then stirred at this temperature for 2 hours. 20 ml of water were added, and the pH was adjusted to between 1 and 3 with about 20 ml of hydrochloric acid (30%) at 10-13° C. After stirring for 5 minutes, the phases were separated. The organic phase was extracted with 10 ml of water. The organic phase was distilled in vacuo until the remaining volume was about 50 ml. It was cooled to 0-5° C. and then seeded with about 0.1-0.2 g of methyl 3-(2-oxocyclopentyl) -2-phenylacetylaminopropionate. A suspension formed after about 10 minutes and was then stirred for 20 minutes. Subsequently, 45 g of diisopropyl ether were added. An easily stirrable suspension formed. It was stirred at 0-5° C. for 30 minutes, then filtered with suction, washed with 2×20 ml of diisopropyl ether (precooled to 5-10° C.) and dried in a vacuum oven at 50° C. 15.95 g (86.8%) of product were obtained.

EXAMPLE 2

Preparation of the Compound of the Formula (II) with R Equal to Methyl Starting from Methyl N-phenylacetylserinate A tank was charged with 20.0 kg of methyl N-phenylacetylserinate. Then 120.0 l of ethyl acetate were introduced into the tank. The suspension was heated to 40-45° C. while stirring. Then a mixture of 4.0 kg of phosphorus trichloride and 6.0 l of ethyl acetate were added from a reservoir to the tank at 40-45° C. over the course of 30-45 minutes and washed into the tank with 6.0 l of ethyl acetate. The reaction mixture was stirred at 40-45° C. for 45-60 minutes. At a maximum jacket temperature of 45° C., 20-25 l of ethyl acetate were distilled out of the reaction mixture in vacuo, removing the excess phosphorus trichloride. The reaction mixture was cooled to 20-30° C. and then 15.0 l of ethyl acetate were added. Then 18.9 kg of triethylamine were added to the reaction tank at 20-30° C. over the course of 15-30 minutes and washed with 5.0 l of ethyl acetate. 20.1 kg of 1-cyclopent-1-enylpyrrolidine were then added to the tank at 20-30° C. over the course of 20-30 minutes. 5.0 l of ethyl acetate were used for washing. The reaction mixture was stirred at 20-30° C. for at least 3 hours. For working up, 25 l of water were added. The reaction mixture was equilibrated at 10-15° C. The pH of the reaction mixture was then adjusted to 2.0-2.5 by adding 30% hydrochloric acid. The reaction mixture was stirred for 10-20 minutes. The phases were then separated and the ethyl acetate phase was mixed at 20-25° C. with 15 l of water and stirred for 10-20 minutes. The phases were again separated. The combined aqueous phases were mixed at 20-25° C. with 15 l of ethyl acetate and extracted for 10-20 minutes. The organic phase is concentrated to a remaining volume of 18-23 l in vacuo at a max. 70° C. The distillation residue was cooled to −3° C. to +3° C. and then seeded with 20 g of methyl 3-(2-oxocyclopentyl)-2-phenylacetylaminopropionate. The mixture was stirred at −3° C. to +3° C. for 60-120 minutes. The product suspension was then mixed with 80.0 l of diisopropyl ether and again stirred at −3° C. to +3° C. for 60-90 minutes. The suspension was isolated on a pressure funnel. The isolate was washed twice with 10.0 l of diisopropyl ether each time. The material was dried at 30-40° C. 13.7 kg of product (purity 95.7%, yield 51.2%) were obtained.

EXAMPLE 3

Hydrolysis of the Compound of the Formula (II) with R Equal to Methyl to Give the Compound of the Formula (III) [Step (A)]

10.8 kg of compound (II) with R=CH$_3$, methyl 3-(2-oxocyclopentyl)-2-phenylacetylaminopropionate, 23.7 l of water and 5.5 kg of sodium hydroxide solution (33%) were introduced into a tank. The reaction mixture was heated to 45° C. and stirred at this temperature for 5 hours. It was cooled to 20° C., and the pH was adjusted at this temperature to pH 6.4 with hydrochloric acid (30%). The reaction mixture was diluted with 30 l of water. The compound 3-(2-oxocyclopentyl)-2-phenylacetylamino-propionic acid (III) which was produced in the reaction and was in the form of a mixture of 2 diastereomeric racemates was processed further as aqueous solution in the following step without further purification.

EXAMPLE 4

Enzymatic Racemate Resolution Using Penicillin G Amidase (Preparation of the Compound of the Formula (V)) [Step (B)]

2.5 kg of polymer-bound penicillin G amidase (PGA450, from Roche diagnostics GmbH, Mannheim, Germany, order number 1414 208) were added to the reaction mixture from example 3 comprising [2RS,3RS]-3-(2-oxocyclopentyl)-2-phenylacetylaminopropionic acid of the formula (III). 77 l of water were used for rinsing. The reaction mixture was heated to 28° C. and stirred at this temperature and at a pH of 6.4 for 5 hours. The reaction mixture was then filtered.

16.2 l of ethyl acetate were added to the reaction mixture, and the pH of the mixture was adjusted to pH 2.2 with hydrochloric acid (30%). After phase separation, the aqueous phase was extracted three times more with 16.2 l of ethyl acetate each time. The aqueous phase comprising the desired product (2S,3RS)-2-amino-3-(2-oxo-cyclopentyl)propionic acid hydrochloride (IV)-HCl, which is in equilibrium through elimination of water with 2,3,3a,4,5,6-hexahydrocyclopenta[b]pyrrole-2-carboxylic acid hydrochloride (V)-HCl, was reacted without further working up in the following reaction.

EXAMPLE 5

Reaction of the Compound (II) with Penicillin G Amidase [Step (BA')]

Compound (II) was dissolved in a mixture of isopropanol and water (50% w/v), and 0.2 M potassium phosphate buffer of pH 8.0 was added to adjust to a final concentration of 60 g/l (II). The reaction mixture was mixed with 0.8 kU of polymer-bound penicillin G amidase (PGA450, from Roche Diagnostics GmbH, Mannheim, Germany, order number 1414208) per g of compound (II) and incubated at 28° C. The reaction was stopped after 24 hours by adding 85% strength phosphoric acid to a pH of 2. The unwanted enantiomers were extracted by extraction with ethyl acetate, and the desired product was present in the aqueous phase.

The reactions of example 4 and as above in example 5 can be carried out in an analogous manner with the penicillin G amidases supplied by Fermenta Biotech Ltd. or Fluka or with other suitable penicillin G amidases.

EXAMPLE 6

Isolation of the Mixture of Compounds (IV)-HCl and (V)-HCl 400 g of a solution of a mixture of (IV)-HCl and (V)-HCl as in example 4 were distilled at 50° C. under a pressure of 30-50 mbar to give an oily residue, which crystallized on standing. The crystals were stirred with 700 ml of acetone at 50° C. for 1 hour, cooled to 0-3° C., stirred for 1 hour, filtered off with suction and washed with 100 ml of acetone. The product was dried in vacuo at 30° C. The mixture of the compounds (IV)-HCl and (V)-HCl was obtained as a pale brown powder, final weight: 46.9 g of pale brown powder.

EXAMPLE 7

Hydrogenation of the Compound (V) to Give the Compound of the Formula (VI) [Step (C)]

The aqueous phase of the working up of example 4 was mixed with addition of 140 g of palladium (5% on activated carbon) and 540 g of activated carbon. A pressure of 10 bar was applied. The temperature was then raised to 80° C. The reaction mixture was hydrogenated at this temperature for 5 hours. For working up, the reaction mixture was filtered. The aqueous phase was adjusted to pH 2 with hydrochloric acid and any by-products were removed by extraction. The aqueous phase contained compound (VI), (2S,3aS,6aS)octahydrocyclopenta[b]pyrrole-2-carboxylic acid, as hydrochloride.

EXAMPLE 8

Isolation of Compound (VI)

206 g of a solution of compound (VI) desalted by electrodialysis were distilled in a rotary evaporator in vacuo at 50° C. over the course of 2 hours until the remaining weight was 110 g. 500 ml of acetone were added to the suspension and it was cooled to 0-3° C. and stirred for 2 hours. Filtration with suction was followed by washing with 50 ml of cold acetone and drying in vacuo at 50° C. 32.6 g of compound (VI) were obtained as a whitish powder.

EXAMPLE 9

Benzylation of the Hydrochloride of Compound (VI) to Give the Hydrochloride of Compound (VII) [Step (D-B.1)]

The aqueous phase of the working up of the hydrogenation described in example 7, comprising 1.76 kg of the compound of the formula (VI), were adjusted to pH 6.3 with 56.5 g of 33% strength NaOH. This solution was filtered, washed with a little water and transferred into an electrodialysis system. The solution was dialyzed at 14 V and a circulation rate of 180-200 l/h for 62 minutes until the current strength no longer fell.

The aqueous desalted solution of compound (VI) was concentrated to a remaining mass of 140 g in a rotary evaporator in vacuo at 40-50° C. 45 g of methanesulfonic acid were slowly added to this solution while cooling in ice at 20 to a maximum of 30° C., and the mixture was stirred for 30 minutes.

The aqueous (VI)-mesylate solution was concentrated to a remaining mass of 140 g in a rotary evaporator in vacuo at 40-50° C. 140 ml of n-heptane were added to this solution. 39 g of benzyl alcohol were added while stirring. The reaction mixture was heated to reflux under atmospheric pressure, and water was removed azeotropically until the rate of azeotropic removal is about 0.3 g/hour. 40.8 g of benzyl alcohol were then metered in over the course of 40 minutes while trapping water. The mixture was stirred under reflux for 2 hours until no more water was trapped. The reaction mixture was cooled to about 10° C., and 187 ml of water were added dropwise. The phases were separated. The upper organic phase was again extracted with 10 ml of water. The combined aqueous phases were mixed with 136 g of ethyl acetate and cooled to 0-10° C. A pH of 10-10.5 was then adjusted with 25 ml of 33% strength NaOH. Stirring at 0-10° C. for 15 minutes was followed by separation of the phases. The organic phase was washed with 15 ml of water. The combined aqueous phases were washed with 20 ml of ethyl acetate. The organic phases comprising the compound (VIII) were combined and diluted with ethyl acetate to 250 g. A pH of 1 was adjusted at 5-10° C. with 23 ml of 30% strength HCl, whereupon compound (VIII), benzyl(2S,3aS,6aS)octahydrocyclopenta[b]pyrrole-2-carboxylate, crystallized as hydrochloride. It was stirred at 0-5° C. for 1 hour, and the product was filtered off with suction and washed with 50 ml of cold ethyl acetate. The product was dried in vacuo at 40° C.

EXAMPLE 10

Preparation of Compound (I) [Steps (D-B.2.1) and (D-B.3)]

10.0 g of (VIII)-hydrochloride from example 9 were introduced together with 40 ml of butyl acetate and 87 ml of water into a 250 ml flask. The pH was adjusted to 10.5 and maintained with 33% strength NaOH while stirring at 20-25° C. The mixture was stirred for 30 minutes until the pH no longer falls. The phases were separated, and the aqueous phase was back-extracted with 5 ml of butyl acetate. The organic phases were combined and concentrated completely to constant weight in a rotary evaporator in vacuo at 50° C.

Compound (VIII), which remained as oil, was taken up in 45 ml of butyl acetate, and 10.6 g of ethyl (2S)-2-[(4S)-4-methyl-2,5-dioxooxazolidin-3-yl]-4-phenylbutyrate (VII) were introduced at 20-25° C. over the course of 30 minutes. The reaction mixture was stirred for 60 minutes. 25 ml of water were added and, after stirring for 10 minutes, the phases were separated. The organic phase was concentrated completely to constant weight in a rotary evaporator in vacuo at 50° C. The remaining oily compound (X), benzyl(2S,3aS,6aS)-1-[2-[(1S)-1-ethoxycarbonyl-3-phenylpropylamino]-(2S)-propionyl]octahydrocyclopenta[b]pyrrole-2-carboxylate, was taken up in 200 ml of methanol. 0.7 g of moist Pd/C (5% by weight was added, and the reaction mixture was hydrogenated under an $H_2$ pressure of 3 bar at 10° C. for 1.5 hours. After removal of the catalyst by filtration, the filtrate was concentrated to 25 g in a rotary evaporator in vacuo at a bath temperature of 20° C., and 75 ml of diisopropyl ether were added. The mixture was cooled to 0-3° C. and stirred for 1 hour, and the crystallized product was filtered off with suction and washed twice with 15 ml of cold diisopropyl ether each time. The compound (I) obtained in this way was dried in vacuo at <30° C.

EXAMPLE 11

Preparation of Compound (X)

9.62 g of compound (VIII) were dissolved in 20 ml of butyl acetate. At 10-15° C., 89.76 g of compound (VII) as 13.9% strength (1.06 M) solution of compound (VII) were added dropwise over the course of 30 minutes. The mixture was stirred for 60 minutes. For working up, 30 ml of water were added, and the pH was adjusted to 11 with 33.2 ml of NaOH (11% strength), and the mixture was stirred for 30 minutes. After phase separation, the organic phase was concentrated completely to constant weight in a rotary evaporator in vacuo at 50° C. 19.0 g of compound (X) were isolated as a viscous oil.

EXAMPLE 12

Preparation of Compound (I) [Step (D-A)]

The reaction mixture from the hydrogenation of compound (V) comprising (VI)-HCl (example 7) was, after filtration of the hydrogenation catalyst, adjusted to pH 10.0-11.0 with sodium hydroxide solution (33%) at 20-25° C. Then 5.1 kg of ethyl 2-(4-methyl-2,5-dioxooxazolidin-3-yl)-4-phenylbutyrate (VII) were introduced. The mixture was stirred at 20-25° C. for 3-4 hours. During this, the pH was kept constant at 10.0-11.0 by adding sodium hydroxide solution. 2.7 l of acetone were added to the reaction mixture. The pH was then adjusted to 5.0-5.2 with hydrochloric acid (30%) at 15-20° C. 50 g of ramipril (I) were used for seeding, and the mixture was stirred for 30-45 minutes. The pH was adjusted to a pH of 4.4-4.6 with hydrochloric acid (30%) and stirred at 15-20° C. for at least 2 hours. The product was isolated on a pressure filter. The filtercake was washed with 11 l of water. Water-moist ramipril (crude) was dried in an oven at <30° C. It was dried to a water content of less than 5%.

EXAMPLE 13

Purification of Compound (I) by Recrystallization 5.42 kg of compound (I) from example 12 with a water content of less than 5% were introduced first. Then 10.0 l of methanol were added. The mixture was heated to 25-28° C. while stirring and stirred at this temperature for 60-120 minutes. The contents of the vessel were then filtered through a pressure filter and washed with 5.0 l of methanol. The solution was concentrated in vacuo at a jacket temperature of max. 30° C., distilling out about 8-10 l of methanol.

27.1 l of diisopropyl ether then added to precipitate the product. The suspension was cooled to 0-5° C. and stirred at this temperature for at least 3 hours.

The suspension was isolated on a pressure filter. The product was washed twice with 5.4 l of diisopropyl ether at 20-25° C. each time and then blown dry. The moist compound (I) purified in this way was dried in an oven at <30° C.

The present invention is explained in more detail by the following claims, which are intended also to be subject matter of the description.

The invention claimed is:
1. A method for preparing ramipril of the formula (I)

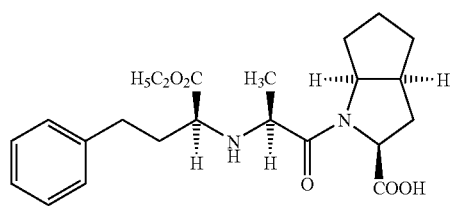

(I)

which comprises
(A) hydrolyzing a compound of the formula (II)

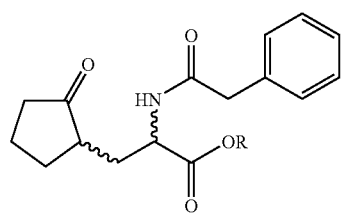

(II)

in which R is $(C_1-C_4)$-alkyl, in a suitable solvent with the addition of one or more bases or acids to a compound of the formula (III)

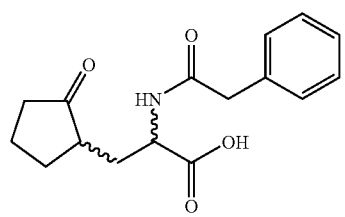

(III)

and then
(B) converting the compound of the formula (III) by addition of penicillin G amidase into a mixture of the compounds of the formulae (IV) and (V)

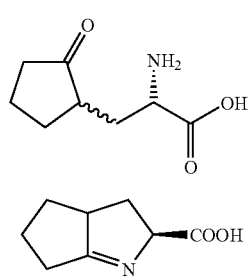

(IV)

(V)

or a mixture of salts of the compounds of the formula (IV) and (V),
or alternatively
(BA') the compound of the formula (II) being reacted with penicillin G amidase and then being hydrolyzed by addition of one or more bases or acids to a mixture of the compounds of the formulae (IV) and (V) or a mixture of salts of the compounds of the formula (IV) and (V),
and then
(C) converting the compound (V) or a salt of the compound (V) from the mixture of the compounds (IV) and (V) or salts thereof by catalytic hydrogenation into a compound of the formula (VI)

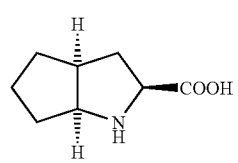

(VI)

or a salt thereof, and then either
(D-A) reacting the compound of the formula (VI) with a compound of the formula (VII)

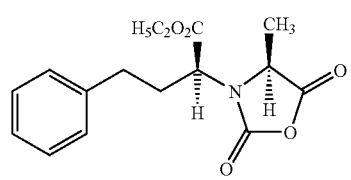

(VII)

to give the compound of the formula (I),
or alternatively (D-B.1) reacting the compound of the formula (VI) with benzyl alcohol to give a compound of the formula (VIII)

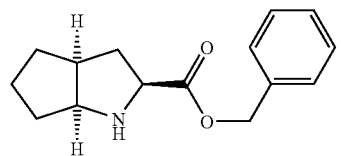

(VIII)

or a salt thereof, and then either (D-B.2.1) reacting the compound of the formula (VIII) either with the compound of the formula (VII) to give a compound of the formula (X)

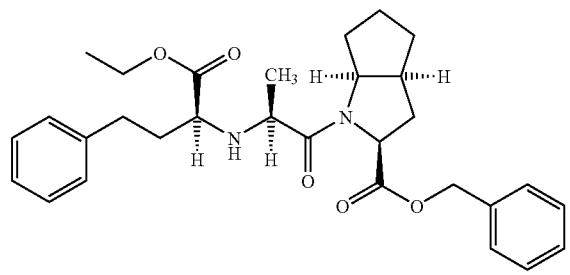

(X)

or alternatively (D-B.2.2) reacting the compound of the formula (VIII) with a compound of the formula (IX)

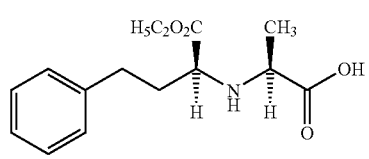

(IX)

to give a compound of the formula (X), and then (D-B.3) forming the compound of the formula (I) from the compound of the formula (X) by catalytic hydrogenation.

2. A method for preparing a mixture of the compounds of the formulae (IV) and (V) or a mixture of salts of the compounds of the formula (IV) and (V)

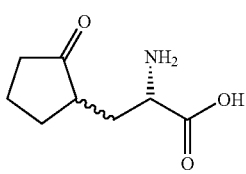

(IV)

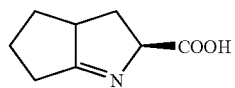

(V)

which comprises treating a compound of the formula (II)

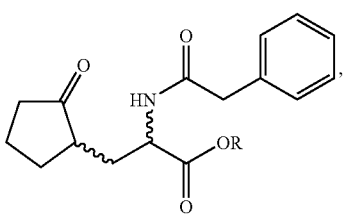

(II)

in which R is $(C_1-C_4)$-alkyl, with penicillin G amidase, and then hydrolyzing with one or more bases or acids.

3. A method for preparing a mixture of the compounds of the formulae (IV) and (V) or a mixture of salts of the compounds of the formula (IV) and (V)

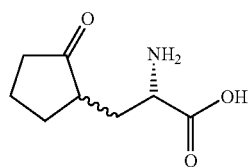

(IV)

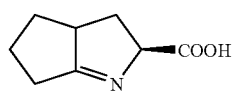

(V)

which comprises treating a compound of the formula (III)

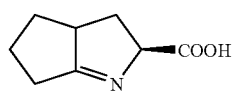

(V)

with penicillin G amidase.

4. A compound of the formula (II)
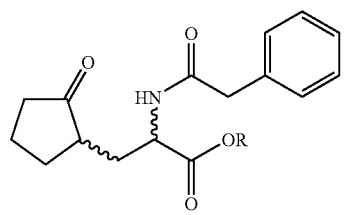
(II)
in which R is $(C_1-C_4)$-alkyl.
5. A compound of the formula (III)
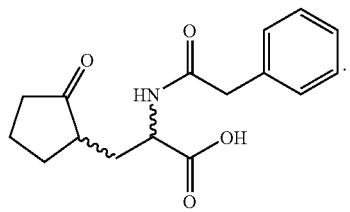
(III)
6. A mixture comprising a compound of the formula (IV)
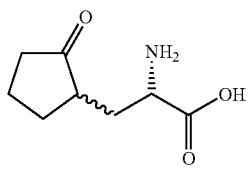
(IV)
and a compound of the formula (V)
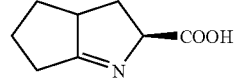
(V)
or comprising a mixture of salts of the compounds of the formula (IV) and (V).
* * * * *